(12) United States Patent
Yan

(10) Patent No.: US 10,537,711 B2
(45) Date of Patent: Jan. 21, 2020

(54) IMAGING COMPETENT, BI-DIRECTIONALLY ARTICULABLE ENDOTRACHEAL TUBES

(71) Applicant: Farbes Medical, LLC, Alexandria, VA (US)

(72) Inventor: WenLiang Yan, Alexandria, VA (US)

(73) Assignee: Farbes Medical, LLC, Alexandria, VA (US)

( * ) Notice: Subject to any disclaimer, the term of this patent is extended or adjusted under 35 U.S.C. 154(b) by 340 days.

(21) Appl. No.: 15/405,927

(22) Filed: Jan. 13, 2017

(65) Prior Publication Data

US 2017/0203075 A1 Jul. 20, 2017

Related U.S. Application Data

(60) Provisional application No. 62/279,327, filed on Jan. 15, 2016.

(51) Int. Cl.
*A61M 25/01* (2006.01)
*A61M 25/00* (2006.01)
*A61M 16/04* (2006.01)
*A61B 1/267* (2006.01)
*A61B 1/00* (2006.01)

(52) U.S. Cl.
CPC ......... *A61M 25/0054* (2013.01); *A61B 1/267* (2013.01); *A61M 16/0418* (2014.02); *A61M 16/0456* (2014.02); *A61M 16/0459* (2014.02); *A61M 16/0493* (2014.02);
(Continued)

(58) Field of Classification Search
CPC .......... A61M 25/0054; A61M 16/0418; A61M 16/0454; A61M 16/0456; A61M 16/0493; A61M 16/0048; A61M 16/049; A61M 16/0495; A61M 16/0497; A61M 16/0461;
(Continued)

(56) References Cited

U.S. PATENT DOCUMENTS

| 3,173,418 A | 3/1965 | Baran |
| 4,150,676 A | 4/1979 | Jackson |

(Continued)

FOREIGN PATENT DOCUMENTS

| WO | 01/34221 A2 | 5/2001 |
| WO | 2014/123473 A1 | 8/2014 |

OTHER PUBLICATIONS

Notification of Transmittal of the International Search Report and the Written Opinion of the International Searching Authority dated Apr. 19, 2017, in connection with corresponding International Application No. PCT/US2017/013427 (9 pgs.).

*Primary Examiner* — Nilay J Shah
(74) *Attorney, Agent, or Firm* — Maier & Maier, PLLC

(57) ABSTRACT

A bi-directionally articulable endotracheal tube includes an articulator with a lever, pivoted on a bite block that, via two attached diametrical wires threaded through the tube wall, controls an articulee with two asymmetric notches sequestrated by three nested, specialized cuffs. A connector having an oval cross-section can effectively house and stopper a video stylet whose flexible tip is nimbly responsive to the articulator. The endotracheal tube can be partially styletted for routine intubation in a direct or video laryngoscopy, or video styletted as a ubiquitous alternative to intubative fiber optic bronchoscope and in combination with a video laryngoscope for dual imaging intubation.

20 Claims, 15 Drawing Sheets

(52) U.S. Cl.
CPC .... *A61M 25/0045* (2013.01); *A61M 25/0147* (2013.01); *A61B 1/00135* (2013.01); *A61M 2205/586* (2013.01)

(58) Field of Classification Search
CPC .............. A61M 16/0465; A61M 16/04; A61M 16/0434; A61M 2039/0255
See application file for complete search history.

(56) References Cited

U.S. PATENT DOCUMENTS

| | | | |
|---|---|---|---|
| 4,685,457 A | 8/1987 | Donenfeld | |
| 6,321,749 B1 * | 11/2001 | Toti | A61M 16/04 128/200.26 |
| 6,553,993 B2 | 4/2003 | Toti et al. | |
| 6,761,171 B2 | 7/2004 | Toti et al. | |
| 7,063,088 B1 | 6/2006 | Christopher | |
| 2008/0092901 A1 * | 4/2008 | Kang | A61M 16/0488 128/207.15 |
| 2012/0073572 A1 | 3/2012 | Li | |
| 2013/0178704 A1 | 7/2013 | Jaime | |

* cited by examiner

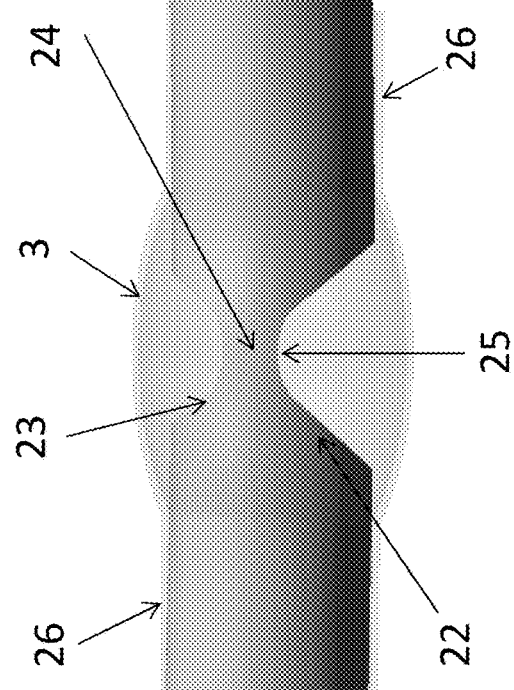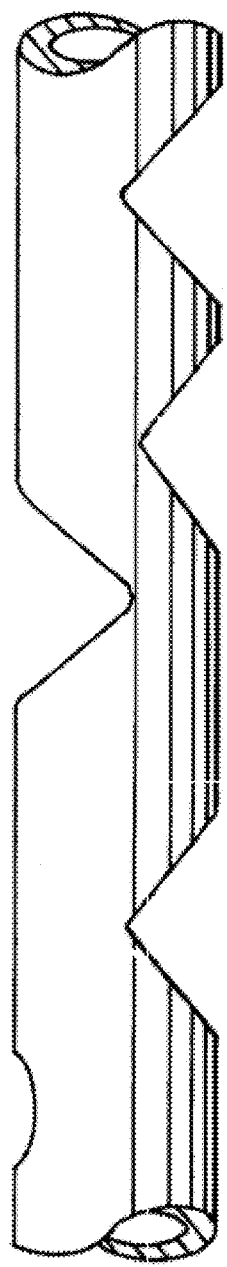

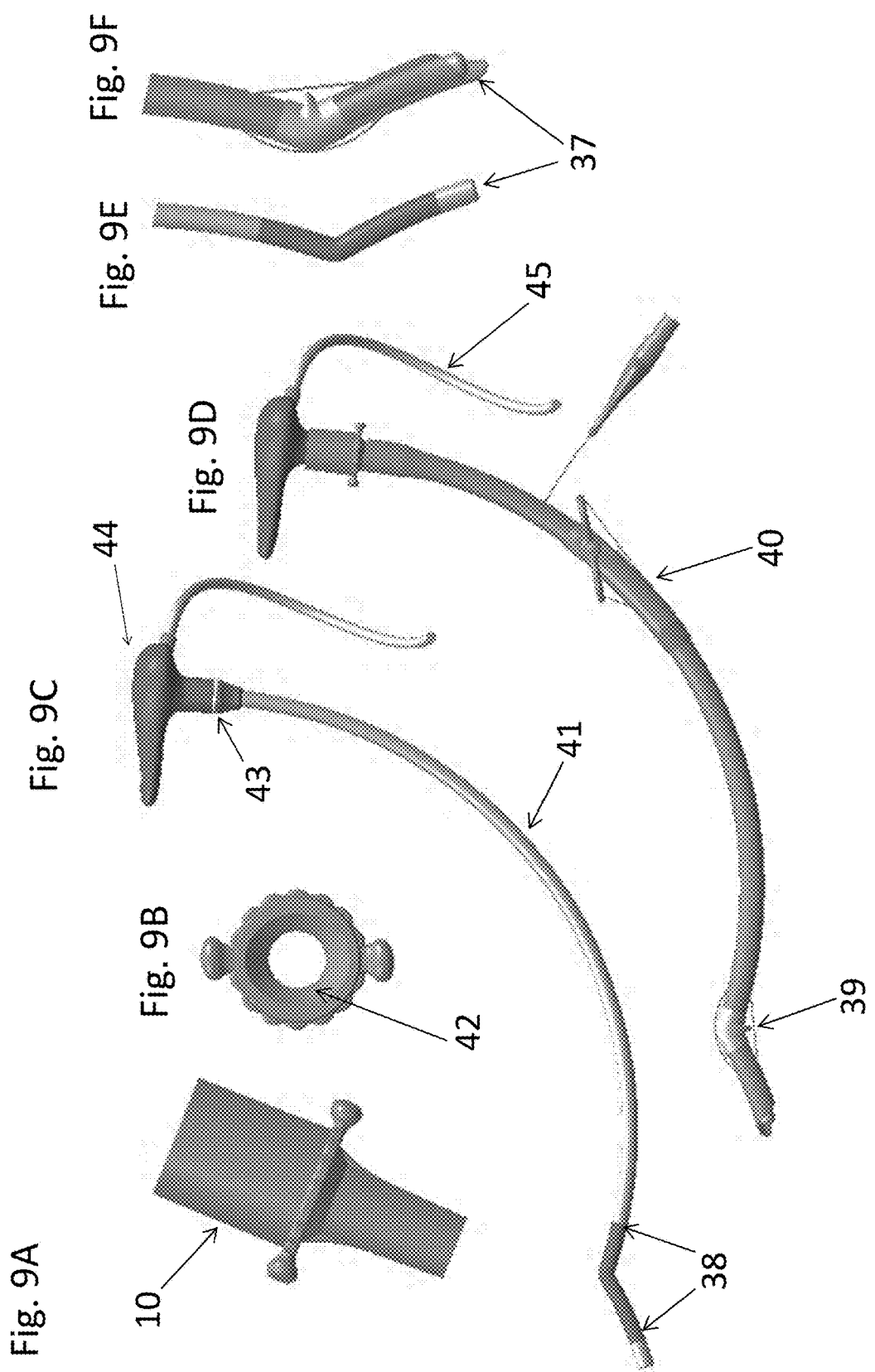

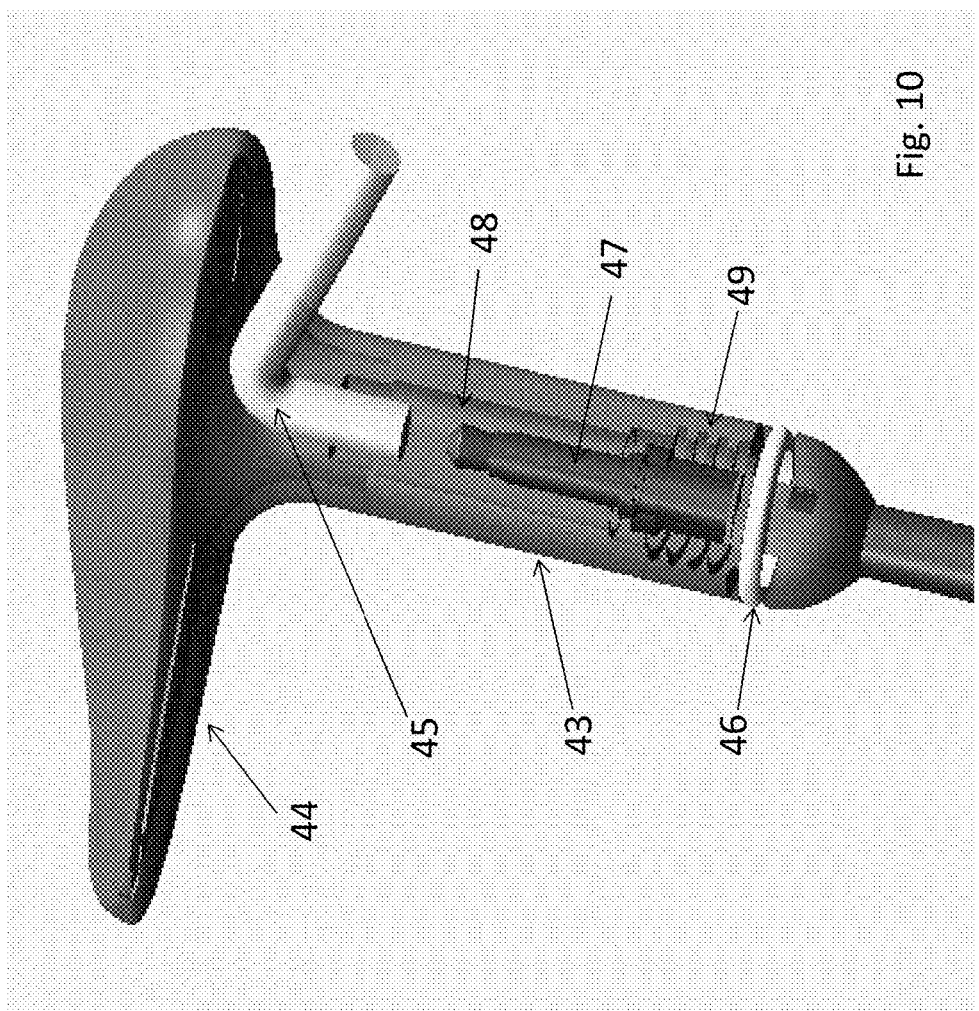

IMAGING COMPETENT, BI-DIRECTIONALLY ARTICULABLE ENDOTRACHEAL TUBES

BACKGROUND

The video laryngoscope has significantly improved tracheal intubation for patients with difficult airways—an anatomical deviation that often results in failed intubation for surgical anesthesia or emergency rescue. In fact, the American Society of Anesthesiologists (ASA) revised its Practice Guidelines in 2013 to include video-assisted laryngoscopy as an initial approach to intubation of the difficult airway.

While revision of the ASA Practice Guidelines affirms a growing trend to establish video laryngoscopy as a routine standard procedure for tracheal intubation, data are conflicting as to whether video laryngoscopy improves clinical outcomes. It was also revealed, in the largest, prospective randomized controlled trial to date, that there are at least 1% of patients who fail to be intubated even under the video laryngoscope and despite an adequate laryngeal view. In clinical anesthesia, this has become a familiar phenomenon known as "can see [the vocal cords] but can't intubate," or CSCI.

Confronting such a challenge, some manufacturers are resorting to the assembly of a multitude of devices, with an interchangeable port connected to a common display monitor (e.g., MultiViewScope by MPI Inc, Airway Total Solution by Acutronic AG, C-CAM/C-HUB by Karl Storz AG). All of which enable practitioners to swiftly disassemble a device failed to intubate and mount on another for a renewed attempt.

The algorithm of intubation underlying such an approach follows that an intubationist usually begins with a conventional laryngoscope, then change to VL if that fails, and finally, as shown in the aforementioned clinical trial and elsewhere, switch to the device most often deployed as the last resort, the flexible (fiber optic) bronchoscope (FOB).

Such a sequence, however, under the duress of rapid oxygen desaturation or life threatening emergency, may become suboptimal, if not irrational. Furthermore, the more attempts an intubationist makes, the higher risks for oral pharyngeal injuries would it lead to. Instead of device switching, it seems that an intubation device should strive for successful intubation in the first attempt at any time.

The higher success of the fiber optic bronchoscope in the most difficult intubations is largely owing to the articulable tip that other devices do not possess. FOB is a flexible imager, whose long, thin shaft may be maneuvered to perform snake-like movements passing through between the vocal cords, on which an endotracheal tube (ETT) can be carried over. Coupled with other tools for biopsy or lavage, FOB, originally developed for the tracheal and bronchoalveolar visualization and treatment, is an overly sophisticated instrument, not optimized and priced for tracheal intubation. Its shortfalls as an intubation device are known as the following.

First, due to its flimsy nature, FOB, en route to the vocal cords, may lose its way during lengthy detours inside some treacherous anatomies such as the piriform fossae, instead of passing over them. Consequently, the intubation time under FOB is significantly prolonged, risking the complications of oxygen desaturation. Additionally, the technique of FOB intubation requires a much longer learning curve to master; and, additionally, it can be afforded by few due to its high price tag, currently about $12,000 apiece. An anesthesia service in a typical 300-bed community hospital in the US may even have only one FOB shared with other departments.

This often results in a crisis mode, when the device is demanded by more than one patient with a difficult airway. Nevertheless, in other environments, such as in poorer developing countries, the cost of the device is prohibitive.

Many inventors have since sought simpler alternatives to FOB either on the stylet that assists the entry of endotracheal tube or directly on the tube itself. In 2002, there was a prospective study conducted by the US National Emergency Airway Registry. With 7,712 patients in 30 hospitals of three countries and among six adjunct devices used, the result showed that a tip-articulable ETT named Endotrol (Mallinckrodt) could surprisingly achieve 83% of the success rate of FOB in rescuing the failed intubation. At present day's price, the former is $1/1,000$ the cost of the latter, while its associated imaging system is $1/100$ the cost.

The Endotrol, also called the "trigger tube", is the first one-directional, tip-articulable endotracheal tube, proposed almost 40 years ago by Isaac Jackson for nasal intubation (U.S. Pat. No. 4,150,676). It has an index finger pulled nylon control wire threaded through the passageway (a hole) inside the ETT wall. In 1986, Roger Donenfeld conceptually extended it to a four-directional articulable ETT by augmenting the Jackson design to four wires running through four holes (U.S. Pat. No. 4,685,457), though no products have ever been realized. It should be noted, however, that the ETT manufacturing process has since vastly advanced; nowadays as many seven passageways (holes) can be created along the wall of an ET tube.

Recognizing that the poor performance of Endotrol results from its unbendable tip, Toti et al adopted the design element of endoscopes, breaking open a notch on the bending point of ETT, whose product, now marketed as EndoFlex, has significantly enhanced the articulating capability of ETT (U.S. Pat. Nos. 6,321,749; 6,553,993B2; 6,761,171B2).

Despite the above improvements, the Endotrol and EndoFlex remain rarely used products among intubationists, and if FOB as the benchmark, the primary shortfalls of the two special ETTs are two-fold: the first is their incapability of two directional articulations. The only articular direction they can attain is that tip upward from ETT's concave line, which is already achievable by a styletted ETT maneuvered with the right hand—whereas intubation via difficult airways such as the anterior larynx or through the nasal cavity demands such ETTs that can also articulate on the opposite, i.e., the convex direction. It is this very direction, for which intubationists sought FOB help in the first place, that is missing in both EndoFlex and Endotrol. Indeed, realizing FOB can never be afforded ubiquitously handy spawned a body of literature by intubationists to explore such ad hoc techniques as "reverse loading" or 180° rotation of ETT, all for coaxing the tube forward to the other direction.

The second is their incompetence at imaging. The operation of EndoFlex is based on a "puller" and Endotrol on a "trigger" mechanism. Both require the thumb blocking the ETT connector, which practically prevents them from equipping an imager (e.g., inserting a video stylet into the tube). Furthermore, this very style of operation also made EndoFlex and Endotrol as devices un-ergonomic to use—since the most efficient and comfortable way to use an ETT, as favored by the overwhelming majority of intubationists, is the style like holding a pen, which simultaneously enables the tube to be imaging competent.

SUMMARY

Exemplary embodiments described herein may disclose an endotracheal tube that bears FOB-like functions. It may combine with a video laryngoscope that may constitutes a dual imaging intubation system. The purpose may be to maximize the chance of initial success in both difficult and routine intubations.

In an exemplary embodiment, a bi-directionally articulable endotracheal tube includes an articulator with a lever, pivoted on a bite block that, via two attached diametrical wires threaded through the tube wall, controls an articulee with two asymmetric notches sequestrated by three nested, specialized cuffs. A connector having an oval cross-section can effectively house and stopper a video stylet whose flexible tip is nimbly responsive to the articulator. The endotracheal tube can be partially styletted for routine intubation in a direct or video laryngoscopy, or video styletted as a ubiquitous alternative to intubative fiber optic bronchoscope and in combination with a video laryngoscope for dual imaging intubation.

BRIEF DESCRIPTION OF THE FIGURES

Advantages of embodiments of the present invention will be apparent from the following detailed description of the exemplary embodiments. The following detailed description should be considered in conjunction with the accompanying figures in which:

FIG. 5A may show a side elevational view of an exemplary embodiment of an articulee with diametric notches, according to the present invention;

FIG. 5B may show a side elevational view of an endotracheal tube with notches according to the prior art;

FIG. 9A may show an exemplary embodiment of an endotracheal tube connector;

FIG. 9B may show a cross-sectional view of an exemplary embodiment of an endotracheal tube connector;

FIG. 9C may show an exemplary embodiment of a video stylet;

FIG. 9D may show an exemplary embodiment of a video stylet inserted into an endotracheal tube;

FIG. 9E may show an exemplary embodiment of a camera sensor of the video stylet;

FIG. 9F may show an exemplary embodiment of a camera sensor integrated into an endotracheal tube;

FIG. 10 may show an exemplary embodiment of a handle of a flexible video stylet;

DETAILED DESCRIPTION

Figure 1:
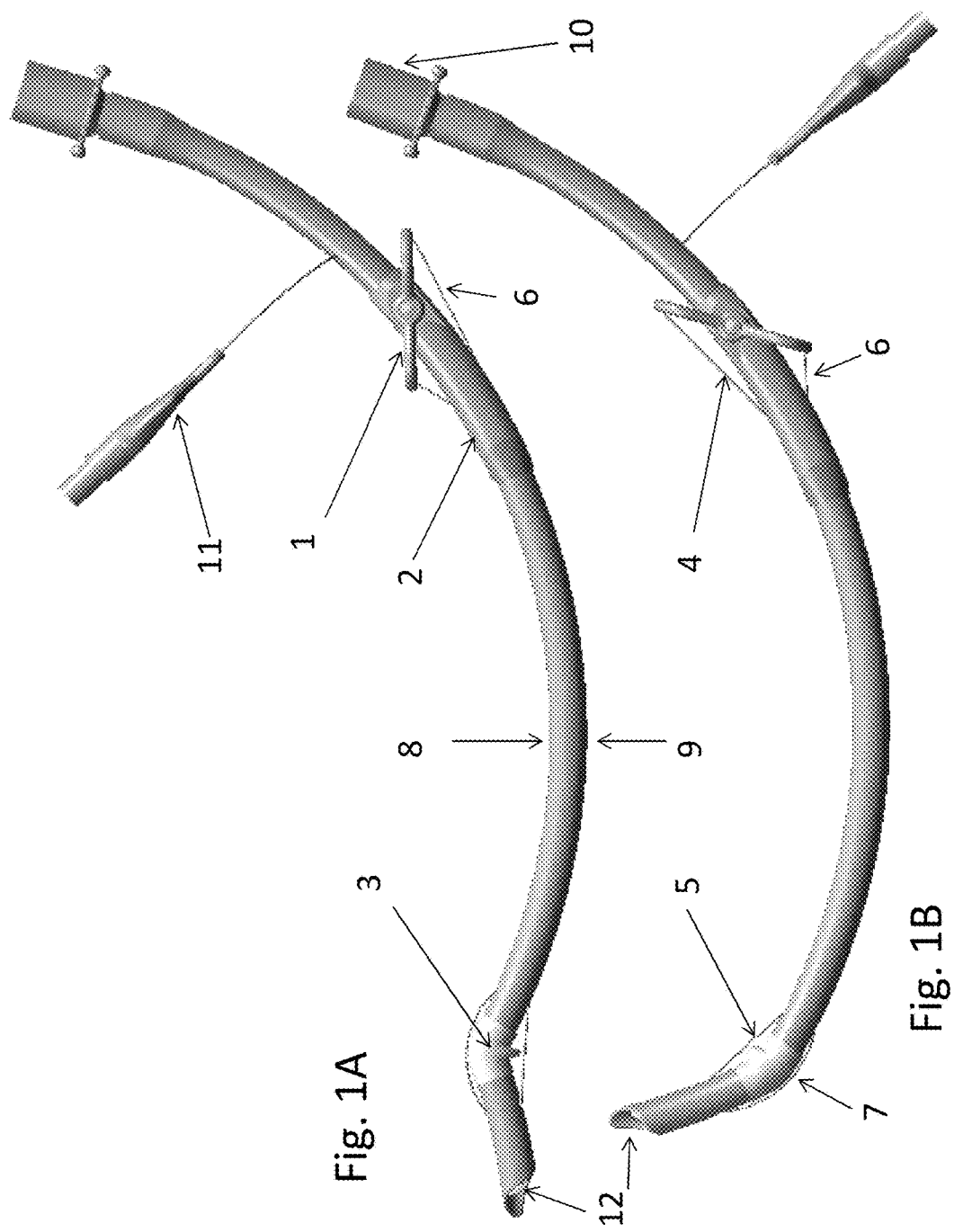
FIG. 1A may show an exemplary embodiment of a bidirectional articulable endotracheal tube according to the present invention, with tip in a downward direction.
FIG. 1B may show an exemplary embodiment of a bidirectional articulable endotracheal tube with tip in an upward direction.
Figure 2:
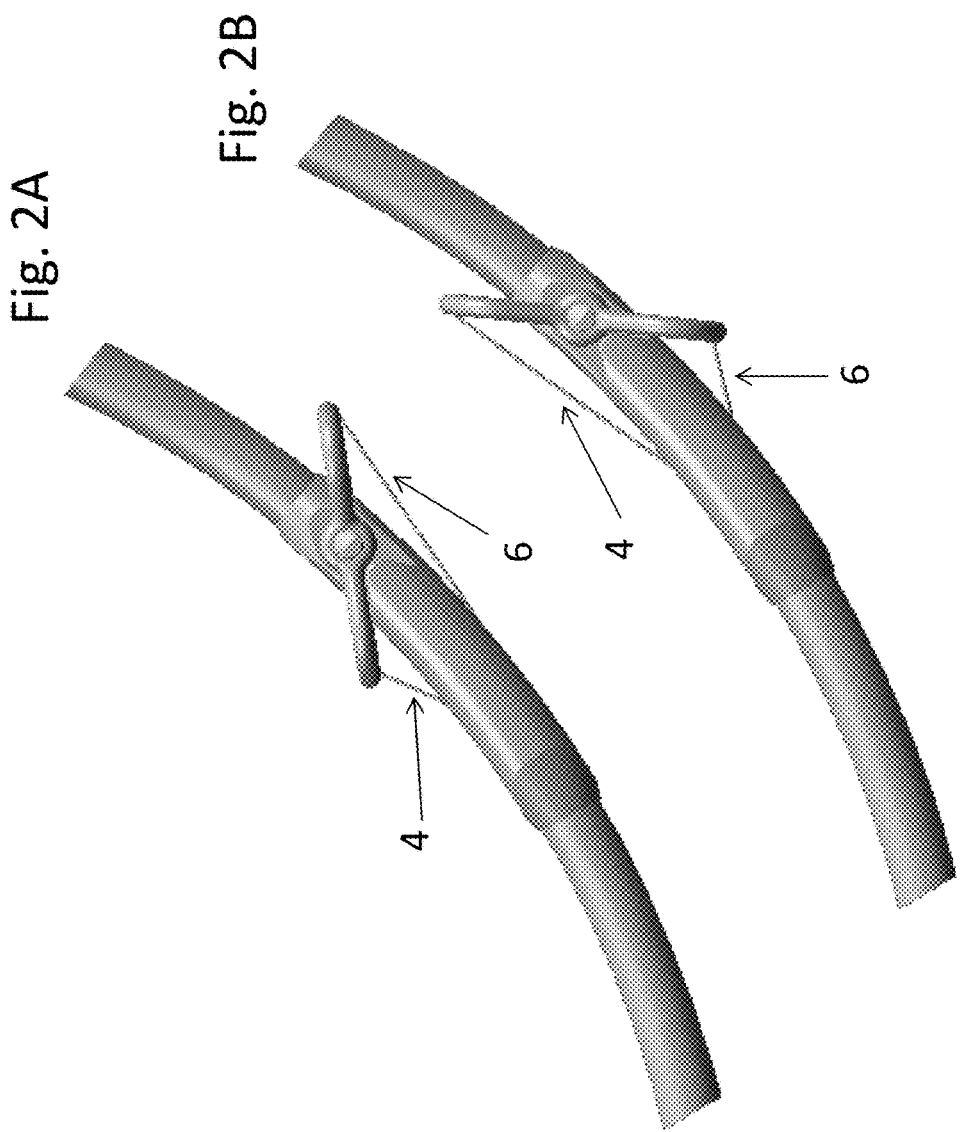
FIG. 2A may show an exemplary embodiment of the articulator of FIG. 1A.
FIG. 2B may show an exemplary embodiment of the articulator of FIG. 1B.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Referring to exemplary FIGS. 1-15 generally, a bidirectional, articulable endotracheal tube may be disclosed. The embodiments described herein may include an endotracheal tube having a video stylet or styled connector, an articulator with bite block, an articulee, and insertion tip. The articulee may facilitate the bending point of the insertion tip, while allowing the main body of the endotracheal tube to remain in its original configuration. The articulee may include two notches that are diametrically positioned and perpendicularly aligned with each other. The arrangement of the notches may preserve the relative integrity and strength of the tube wall at the articulee, while permitting bidirectional tip bending. The articulator may control the articulee. The bite block of the articulator may be secured along the length of the endotracheal tube to prevent a patient from constricting the lumen or tube passageway. The bite block may be slidable along the length of the tube or may alternatively be secured at a predetermined position. In other exemplary embodiments, the endotracheal tube may not contain a bite block. In some exemplary embodiments, the endotracheal tube may extend the design to the nasal and oral RAE tubes by a connector that adds the lever of articulator. The insertion tip may feature a water-drop shape to preserve the accuracy of aim. The tubes may be competent for imaging.

Still referring to the FIGS. 1-15 generally, an endotracheal tube may be a long, flexible tube with two ends: a patient's end may be placed inside the trachea and a machine's end may be connected to a ventilator. The endotracheal tube may have different predetermined diameters according to the standard of clinical usage. Such tubes may have ultrathin steel cable spirally wired on the surface of its interior wall and throughout the entire tube length except for the segment of articulee and endotracheal tube insertion tip, whereby the cable may create a reinforced endotracheal tube. This configuration may prevent the tube from crushing or deformation.

The tube may have a curved body, with a concave and convex side, which correlate with patient's anterior and posterior side, respectively. The tube may have three longitudinal passageways with a predetermined diameter, on the 12, 2, and 6 o'clock position of its cross-sections. The tube may have two notches on the tube's concave and convex side, respectively, wherein they cut through the passageways as well and wherein the tips of the opposing notches point to each other separated by two predetermined spacers on the tube wall. The tube may have a very thin, plastic membranous wrap, whose edges are glued to the surrounding wall of the notches. This may seal the openings of the notches.

The tube may have two elastic polymeric or ultrathin steel wires running through the 180° opposing passageways on both concave and convex sides. The tube may have wires start from the tip of the tube's patient end, where the wires, passageways, and tube wall are firmly glued together, then exit and re-enter the passageways via a pair of holes spanning the membrane-sealed notches. The tube may have a second thin plastic, membranous wrap, whose edges are glued to the tube wall flanking the holes on the passageways. This may prevent air leakage by sequestrating the holes, while permitting the free movements of the wires. The tube may have a third plastic membranous wrap, larger and longer, also spanning the notches. The membranous wrap may have one edge, near the tip of tube's patient end, glued on top of the same edge of the second membranous wrap, and its other edge, on the other side of the notches, glued to the outside of the same edge of the second membranous wrap. This may create a space to allow the 2 o'clock passageway to open up inside. This may allow for air to be injected to inflate the wrap as a "cuff" to seal the tracheal wall.

All endotracheal tubes must have a connector for linking the device to a ventilator via an intermediate breathing circuit. A connector may be a short plastic tube with two ends of different diameters, whose dimensions follow the international standard. One end of the connector may have a smaller external diameter that matches the internal diameter of the endotracheal tube; this may allow it to be inserted into the endotracheal tube's machine end. The other end of the connector may have a larger external diameter that connects the endotracheal tube to the ventilator. The internal shape of the larger end may be oval and may match and securely house an inserting video imaging stylet. The handle of the stylet may have a base stem shaped as an oval.

The tip of patient's end may have a bevel facing the left vocal cord of patient. The brim of the bevel, on the convex side of the tube, may be significantly trimmed in the shape of a smooth letter U with a shorter right arm. In such a configuration, the retained bevel on the tube's concave side may enable better aiming of the tube towards the vocal cords, while the trimmed brim on the tube's convex side may prevent its edge from bumping and dislocating anatomic structures such as the arytenoid cartilages.

Referring to exemplary FIGS. 1A and 1B, a bidirectional articulable endotracheal tube may be disclosed. The bidirectional articulable endotracheal tube may include an articulator having three main components: a lever 1, a bite block 2 and a pair of control wires 4, 6. The lever 1 may be pivotably secured to the bite block 2 by a pair of symmetric pivots disposed on two opposing sides thereof 2. The pair of control wires 4, 6 may be diametrically threaded into the endotracheal tube wall, and may actuate manipulation of the insertion tip 12. A practitioner may grip the lever 1 with a right index finger and thumb, and force rotation of the lever 1, thereby initiating articulator action.

The articulee may include four main components: control wires 5, 7, asymmetric notches, a bulge, patterned inner cuff 3, and a second membrane cuff 27. The control wires 5, 7 may extend from control wires 4, 6 respectively, exiting and reentering the tube wall and spanning over an opposing pair of asymmetric notches 22, 23 (shown in FIG. 5A). The bulge, patterned inner cuff 3 may sequestrate the notches to prevent anesthesia gas leaks, and the second membrane cuff 27 may sequestrate the openings of wires 5, 7 to prevent air leaks from standard endotracheal tube cuff 28 (shown in FIG. 7). Here, the weakened tubular wall, due to notches 22, 23, may create a hinge effect permitting the insertion tip 12 to bend in response to the articulator. Further, it may be appreciated that the integrity and strength of the tubular wall, in the presence of the notches, is almost restored in a different format in an exemplary embodiment by three nested membranous cuffs, together with the control wires. The aforementioned spacers alone can withstand numerous and repeated bending without failure or compromising the structure.

The entire force of articulation is anchored on the two diametric pinpoints at the insertion tip 12, wherein control wires 5, 7 terminate and wherein they are securely bound with the tube wall by physical or chemical means. The endotracheal tube may contain concave 8 and convex 9 sides. Connector 10, coupling the endotracheal tube to the breathing circuit of a ventilator, can house an imager (shown in FIG. 9). A pilot balloon 11 for the standard cuff of the endotracheal tube may also be incorporated.

Referring to exemplary FIGS. 2A and 2B, an endotracheal tube having an articulator with wiring may be disclosed. As depicted in FIG. 2A, when right index finger and thumb coordinate to press down on the pivotal lever 1, the conjugated force exerts through two wires 4, 6 and consequently wires 5, 7 to effectuate insertion tip 12 moving convexly (opposite the endotracheal tubing concave side 8). FIG. 2B may show the opposite forces exerted on the lever 1, which may shift insertion tip 12 in a concave direction. Once the intubation succeeds, the strings attached to the lever 1 may be severed off with a scissors, and the lever 1 either be dislodged, permissible by temporary removal of the connector, or left in situ serving as an anchor point for taping the tube at the mouth corner. The lever 1 can be color coded to differentiate tubes with various diameters. The bite block 2 may be curved conforming to that of standard endotracheal tube, with a predetermined length that allows sufficient leeway for biting with minimal compression of the oral tissues. It may be made of rigid polymer with elastic surface, whose material characteristics can both withstand tube-crushing bite yet also prevent teeth crashing injury.

Figure 3:
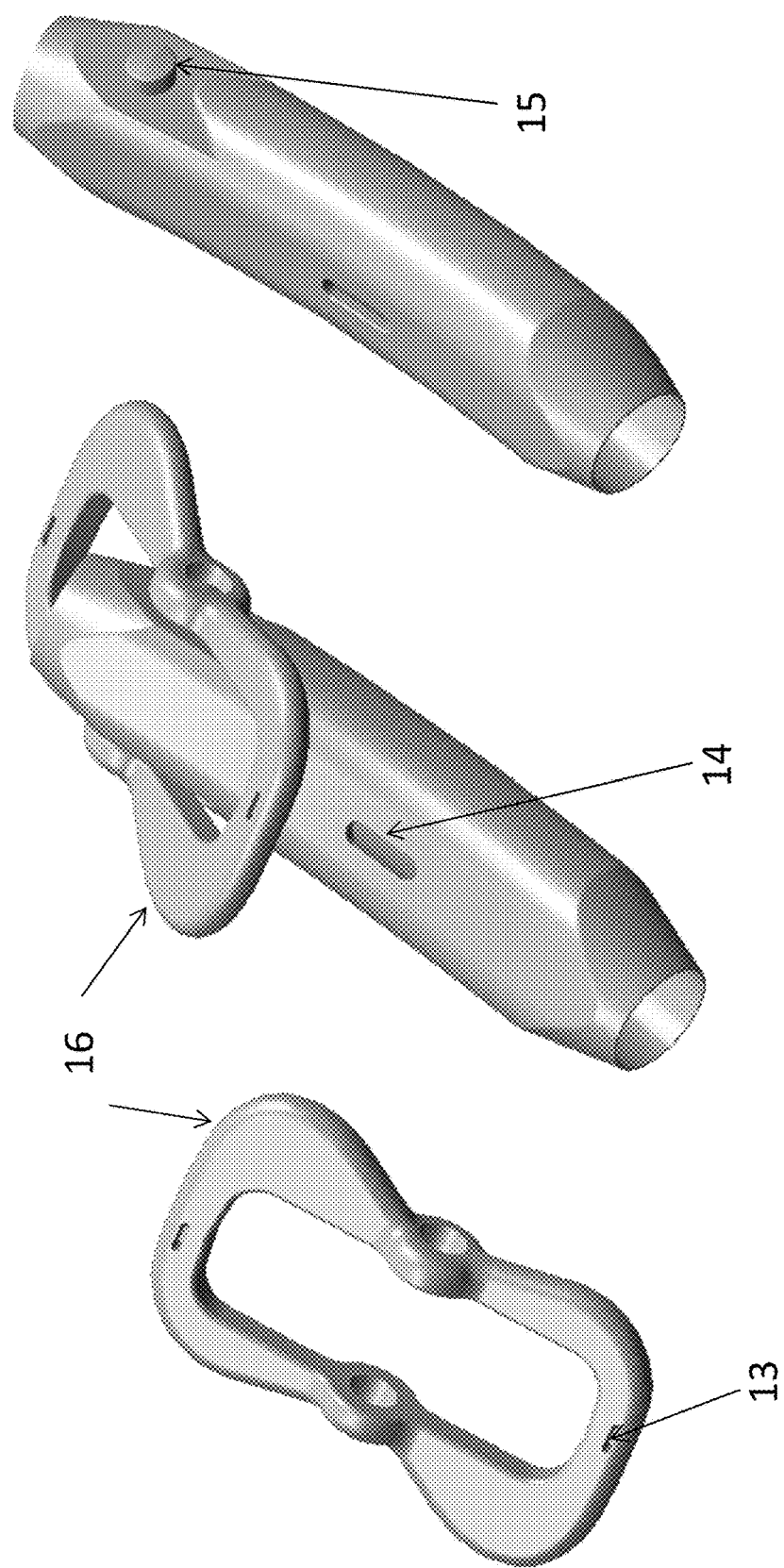
FIG. 3 may show an exemplary embodiment of the assembly components of an articulator.

Referring to exemplary FIG. 3, the assembly components of an articulator may be disclosed. The components of the articulator may include the lever 1 and the bite block 2. Wires 4, 6 may exit the bite block 2 to be attached to the lever 1. The lever may control the bi-directional movements of the tube's end. The lever can be made straight, or curved, like a bow to increase its leveraging power. The lever 1 may be removable, shaped in a rectangular rim constructed from plastic; the centers of the two long sides of the rectangular rim may be enlarged to form a ring. The ring may match the diameter of the fulcrum and lock into it reversibly, and the centers of the two short sides of the rectangular rim may firmly attach to the wires.

The wires may attach to lever 1 at one of two symmetric points 13 located on the convex surface of lever 1. The wires can be either glued or tied to the points 13 on the rim of lever 1. Symmetrical slits 14, on the concave surface of the bite block 2, may allow control wire 4 to pass therethrough and enter passageway 18 (shown in FIG. 4) inside the tube wall. Wire 6 may enter through an opposing symmetrical slit 14, locating on the convex side of endotracheal tube. For the ease of articulator assembly in manufacture, the center slit 14 can be enlarged and shaped in any manner as would be deemed fit by a persona having ordinary skill in the art. The lever 1 may be mounted on pivots 15 and thereby secured to the bite block 2. The lever 1 may be molded to provide ergonomic touches 16, whereby the thumb and index finger can comfortably press to operate lever 1.

In some exemplary embodiments, the tube may have a bite block 2 of plastic having a predetermined length and position along the axis of the tube. The bite block may be made from a single piece or two pieces of plastic that are assembled together by means of mortise-tenon joints. The bite block 2 may be materially harder and more rigid than the endotracheal tubing. The block 2 may longitudinally wrap the tube and may have an oval-shaped cross-section. Two relatively flat sides of the bite block 2 may be surfaced on the tube's concave side and convex side. The bite block 2 may have flat sides that have an open slit 14 on its axis center, and the wires 4, 6 may exit from the slits 14. The tube may have a relatively flat side of the oval contacts patient's teeth as a bite block. The bite block may prevent the biting teeth to crush the tube and may ensure a non-restricted airflow. The bite block may further have two fulcrums, with a predetermined diameter, that may be centered on the non-flat sides of the bite block. The fulcrums may be situated proximate the machine's end of the bite block.

Figure 4:
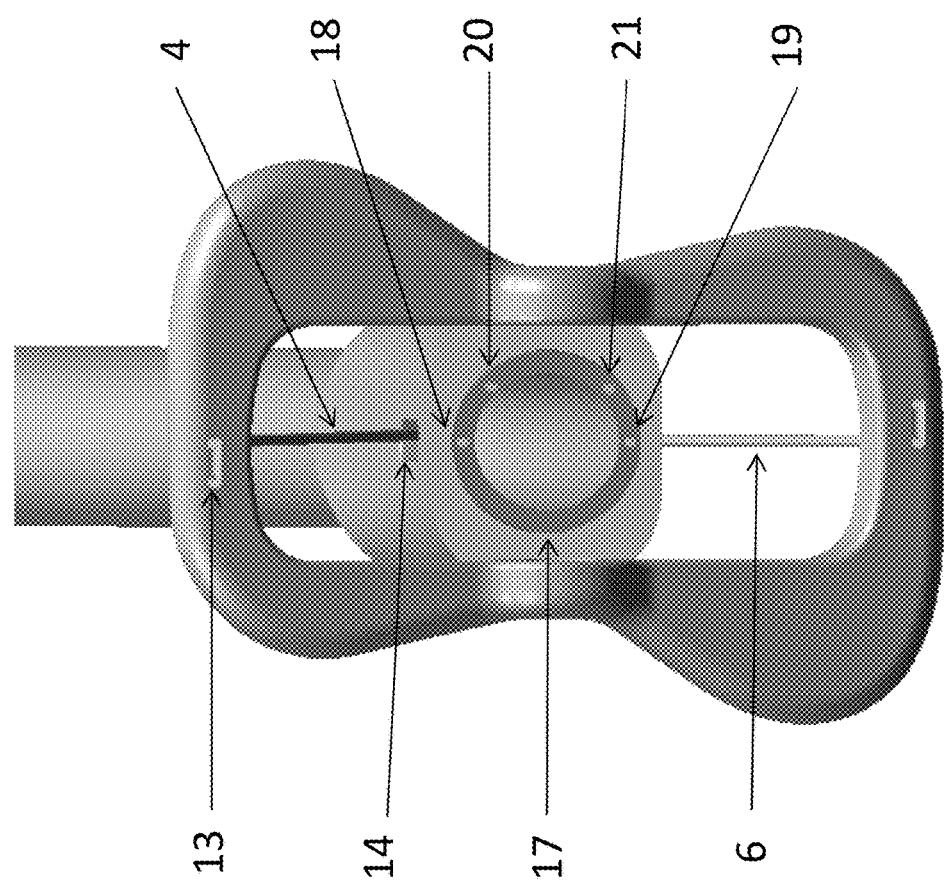
FIG. 4 may show a cross-sectional view of an exemplary embodiment of an articulator in an assembled state.

Referring to exemplary FIG. 4, a cross-sectional view of an articulator in an assembled state may be disclosed. The lever 1 may be secured to control wires 4, 6, which pass through slits 14 on the bite block to enter passageway 18, 19 respectively. Opening 20 may be for pilot balloon tubing that inflates standard cuff 28 (shown in FIG. 7). Opening 21 may be for a standard X-ray tracer line that runs through the entirety of the tube length and may be filled with radio opaque material so as to enable traceable radiology. Opening 21 may alternatively be placed on the left of passageway 19 to avoid the over concentration of passageways on one side of the endotracheal tube. Surface 17 may be a side face of the endotracheal tube, between the concave and convex faces, wherein standard depth marks of tube insertion are routinely printed. For the depth marks to be observable, the bite block 2 may need to be constructed from a transparent material, such as transparent polymer.

Referring to exemplary FIG. 5A, a side elevational view of an exemplary embodiment of an articulee with diametric notches may be disclosed. The articulee may include a pair of diametric notches that weaken the tubular wall to cause articular bending. The diametric notches may be asymmetric, a deep notch 22 on the convex side and a shallow notch 23 on the concave side of the endotracheal tube. Their pointing bottoms may be separated by a pair of spacers 24 on either side, which act as a hinge to pivot the bidirectional bending of endotracheal tip 12. The bottom of each notch 25 must be in round shape to minimize the tearing effect of a sharp V bottom in articular hinging. The notches 22, 23 may be sequestrated by a bulge, patterned inner cuff 3, made of thin and elastic polymeric membrane that can resiliently retain its bulged shape. The tubular inner cuff 3 may have two symmetric ends 26, flanking the bulged central portion, that match the outer diameter of endotracheal tube; sealing off ends 26 onto the tube wall can prevent anesthesial gas leak from inside the endotracheal tube lumen.

Because of the standardized curvature of an endotracheal tube, stronger force may be required to articulate its tip convexly. Thus, in some exemplary embodiments, the endotracheal tube may have notches that have two different sizes. The notch on the convex side may be larger and deeper, cutting into approximately half of the circumference wall of the tube, which allows, the user to overcome the usual stronger resistance to moving the patient end of tube towards the convex side. The other notch may be relatively smaller and shallower cutting. The two pointing tips of the notches may be separated by at least 1-3 millimeters, depending on the outer circumference, wall thickness, and polymeric properties of the tube, so as to preserve the integrity and strength of the wall.

The endotracheal tube may have a first thin membrane that has a patterned shape for sealing the notches beneath the wires. The membrane may have a mid-section bulging out above the notches when its two edges are glued outside the notches. The bulging cover may prevent the membrane from trapping into the notches to form a narrowed airway inside the tube.

The tube wall in notch areas may be weakened particularly by the larger notch on the convex side of the tube. The weakness may further enhance and empower the controlling mechanism to move not just the tube but also the content inside the tube. For example, this may be a video stylet, wherein the stylet may have a flexible printed circuit board positioned to span the notch areas. The video stylet may perform video imaging of relevant anatomies and pathologies during intubation, as the terminus of the tube on the patient end may move bi-directionally by the controlling mechanism and further multi-directionally by hand maneuvers.

FIG. 5B may show the configuration of notches according to prior art (U.S. Pat. No. 6,553,993) for a bi- or multi-directional articulable endotracheal tube. Tests have shown that the multi-notch design, as depicted in FIG. 5B, would make an impotent articulee, poorly responsive to articulator if placed convexly, while unwarranted or unnecessary if placed concavely. Nor is it possible, with the design as depicted in FIG. 5B, to be sequestrated within such a space as narrow as inside a standard endotracheal tube cuff, nor is it possible to manufacture.

Figure 6A:
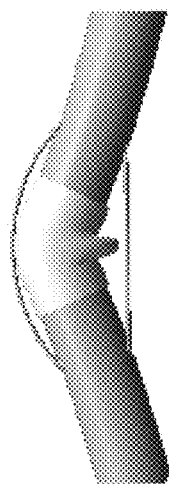
FIG. 6A may show an exemplary embodiment of an inner cuff in a bent configuration.
Figure 6B:
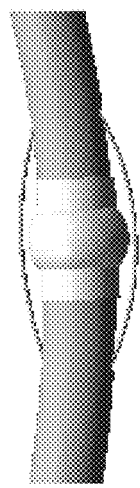
FIG. 6B may show an exemplary embodiment of an inner cuff in a relaxed state.
Figure 6C:
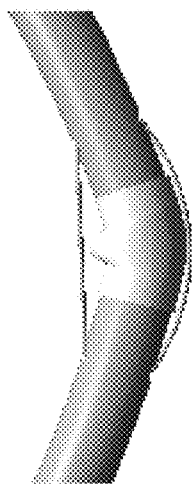
FIG. 6C may show an exemplary embodiment of an inner cuff in a bent configuration.
Figure 6D:
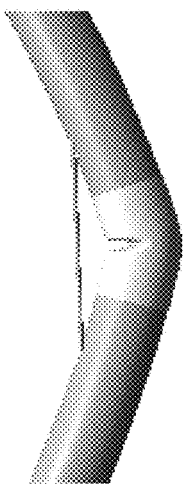
FIG. 6D may show the bending of an EndoFlex inner cuff according to the prior art.

Referring to FIGS. 6A-C, an exemplary embodiment of an inner cuff may be disclosed. When bent in either a concave or convex direction, the bulge, patterned inner cuff does not create any membrane invagination (as shown in FIGS. 6A and 6C). FIG. 6B depicts an exemplary embodiment of the inner cuff in a relaxed, neutral state. The prior art when bent, as depicted in FIG. 6D, shows significant membrane invagination occurring.

Figure 7:
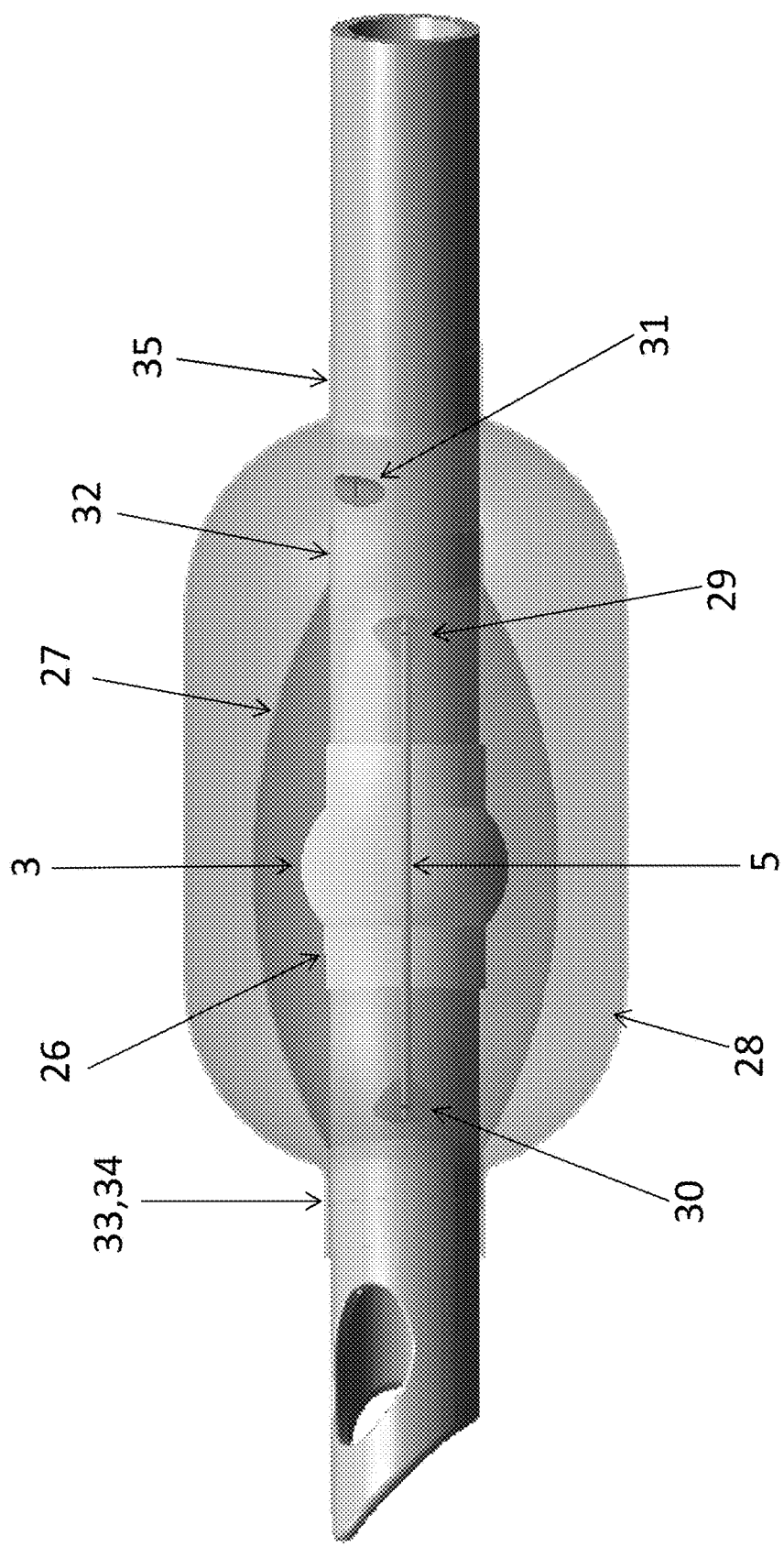
FIG. 7 may show a perspective view of an exemplary embodiment of an articulee.

FIG. 7 may illustrate a perspective view of an exemplary embodiment of an articulee having nested sequestrating cuffs and their sealing points on the tube wall. To effectuate the action of articulator, control wire extensions 5, 7 must exit the tube wall, diametrically encompassing over inner cuff 3 and exerting force on notches-weakened tube wall. Consequently, the four openings, wherein the wires exit and reenter the tube wall, 29, 30 on the concave side and two more symmetrically at the convex side, need to be sequestrated—otherwise their passages to the open air would defeat the standard cuff inflation to seal the trachea for intubation. Thus, a second thin membrane cuff 27 must be created to isolate control wires 5 and 7 and their wall openings 29 and 30 (other two not shown here), which, along with inner cuff 3 within, are all nested inside standard endotracheal tube cuff 28.

FIG. 7 may also illustrate the care that must be exercised to place all tubular cuffs' sealing ends—lest they hamper the free movements of control wires and thus the functions of articulee. Seals 26, the flanking edges of bulged inner cuff 3 and its covered notches below, are inside openings 29, 30 and their convex counterparts; for the second cuff 27, one of its seals 32 must be in between opening 29 and pilot balloon tube opening 31, which is between second cuff 27 and standard endotracheal cuff 28; seal 33 of cuff 27 and seal 34 of cuff 28 are overlapped at the terminal of endotracheal tube. Additionally, it should be noted that once reentered inlet 30 and its convex counterpart, control wires 5, 7 will be securely bound to become the anchor points of force for the entire articulating endotracheal tube.

Figure 8:
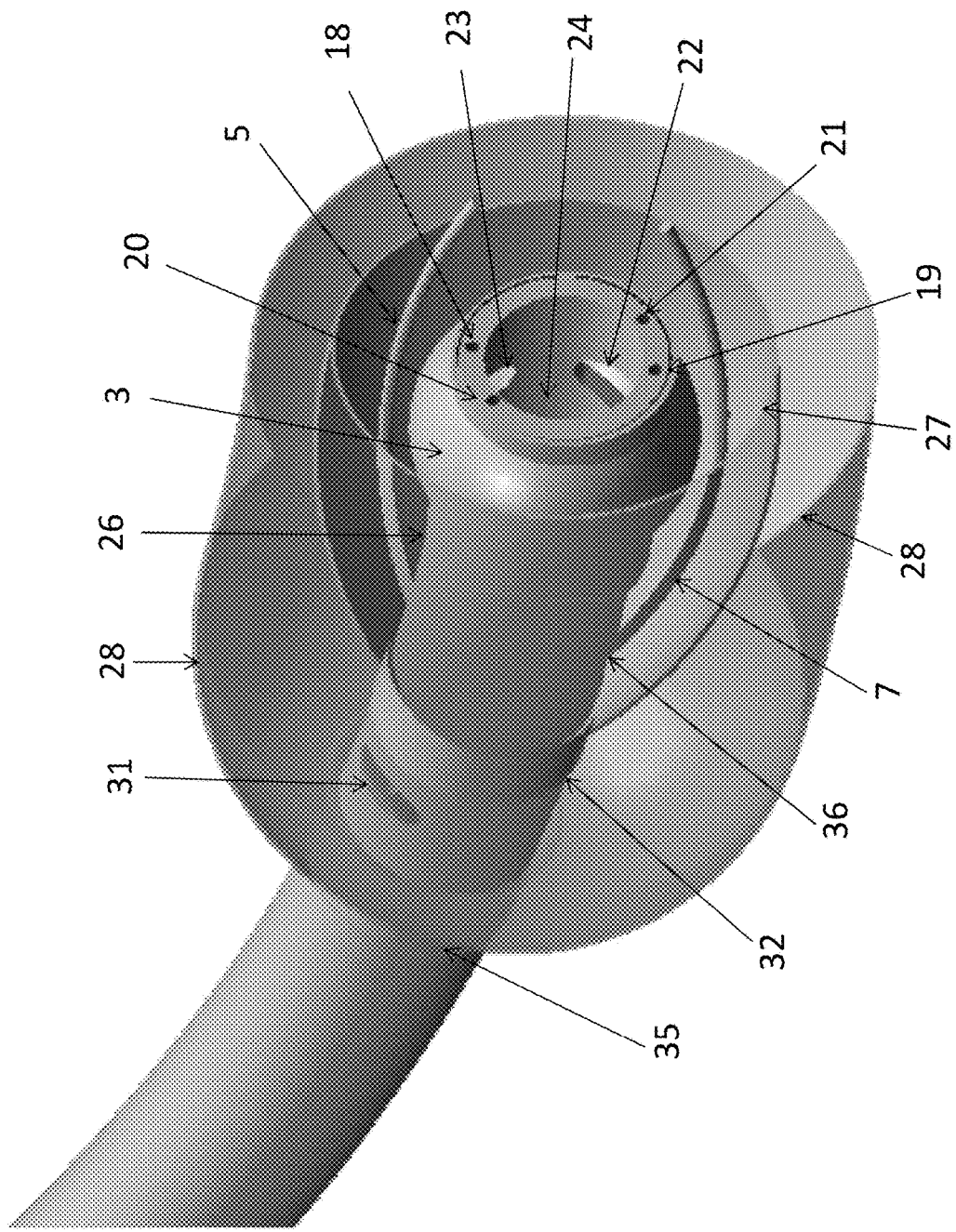
FIG. 8 may show an enlarged, cross-sectional view of an articulee.
Figure 11A:
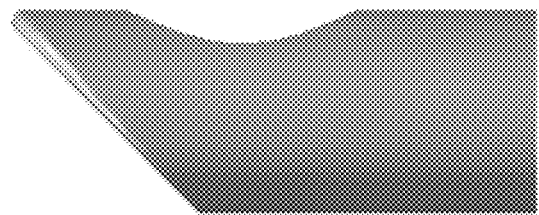
FIG. 11A-D may show exemplary embodiments of an endotracheal tube tip.
Figure 11B:
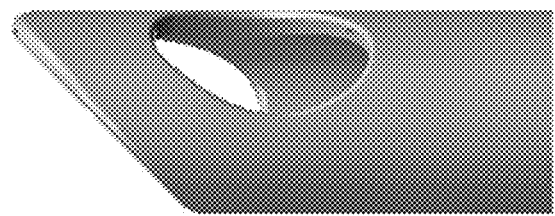
Figure 11C:
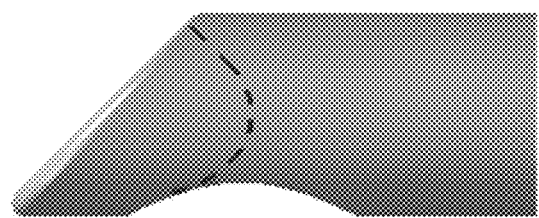
Figure 11D:

Referring to exemplary FIG. 8, an enlarged, cross-sectional view of an articulee may be disclosed. From the inside out, deep and shallow notches 22, 23 may be illustrated with one of the spacers 24. Diametric passageways 18, 19 may be inside tube wall. Two more passageways are illustrated for pilot balloon tubing 20, and radio opaque line 21 (alternative position to that in FIG. 4). Additionally, the articulee may include inner cuff 3 with one of its seals 26, control wires 5, 7, exit opening 36 for wire 7, second membrane cuff 27 (dissected open), second membrane cuff seal 32 (in between wire 7 opening 36 and pilot balloon tube opening 31); and standard endotracheal tube cuff 28 (dissected open) with one of its seals 35.

Referring to exemplary FIGS. 9A-F, an exemplary embodiment of an endotracheal tube and its parts may be disclosed. In the attempt to create a ubiquitous alternative to expensive flexible fiber optic bronchoscope (FOB), a video stylet in FIG. 9C customized for the application is constructed, wherein the camera sensor 37 (FIGS. 9E, F) and its microcontroller are separated by a FPCB (flexible printed circuit board) 38 (FIGS. 9C, E) that registers with articulee 39, so that when the video stylet is inserted into the endotracheal tube as in FIG. 9D, its FPCB segment in concert with articulee 38 responds nimbly to articulator 40. The video stylet in FIG. 9C may have a rigid body 41 with the same curvature as the endotracheal tube. The interior of standard endotracheal tube connector 10 (FIG. 9A) for the breathing circuit may be changed to an oval shape 42 (FIG. 9B) that matches the shape of stem 43 of pointed handle 44 on video stylet—together with an O-ring 46 on stem 43 (FIGS. 9C, 10) these design features secure the video stylet in a proper polarity, wobble free housing, fine depth stopper, for effective imaging as a FOB alternative.

Additionally, a data cable 45 may link video stylet to a display monitor. The video image transmission mode can be wired as the cable links described herein, or may alternatively be transmitted wirelessly, via Bluetooth or WiFi communication protocols.

Operationally, intubation with fiber optic bronchoscope (FOB) may be pursued in two steps, i.e., FOB may maneuver to find the vocal cords first, and then load the endotracheal tube into the trachea next. The invention disclosed herein may combine the two steps into one. A video stylet that registers with articulee may be inserted into the endotracheal tube. The stylet imager here, in contrast to the intubative bronchoscopy, may be maneuvered by an articulable tube to assist in finding the vocal cord, thereby completing intubation in one step.

Now referring to exemplary FIG. 10, a flexible video stylet with handle may be disclosed. The flexible video stylet can be made to have its handle 44 with stem 43 and its body 41 separable so that the latter be subject to sterilization after each use. In one embodiment, the matching oval stem 43 and body 41 can be disjoined electronically by a pair of connectors, such as earphone plug 47 and jack 48, above O-ring 46, as in FIG. 10. The joining of such a connection can be in the form of a screw pair 49, fastened in the same oval shaped handle stem 43.

Referring to exemplary FIGS. 11A-D, an endotracheal tube tip may be disclosed. To improve the maneuver of the tube, modification has been made to tip; the bevel underside may be pruned to a concave configuration (dotted portion in FIG. 11C). This may lessen the chance that tip's underside stumbles upon such anatomical structures as arytenoid cartilages en route to the vocal cords. On the other hand, the vocal-cords aiming specialty (FIGS. 11A, B) of its left-facing bevel on the upside may still be retained.

Figure 12:
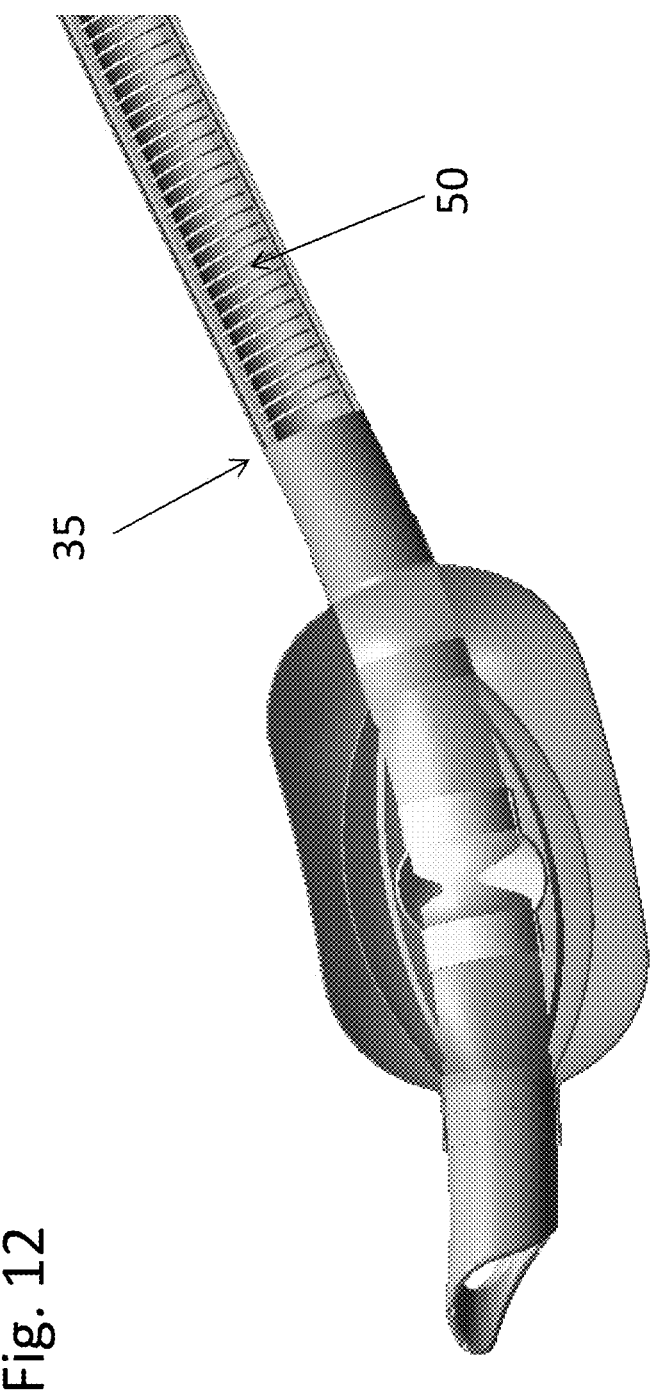
FIG. 12 may show an exemplary embodiment of a reinforced endotracheal tube with articulee.
Figure 13:
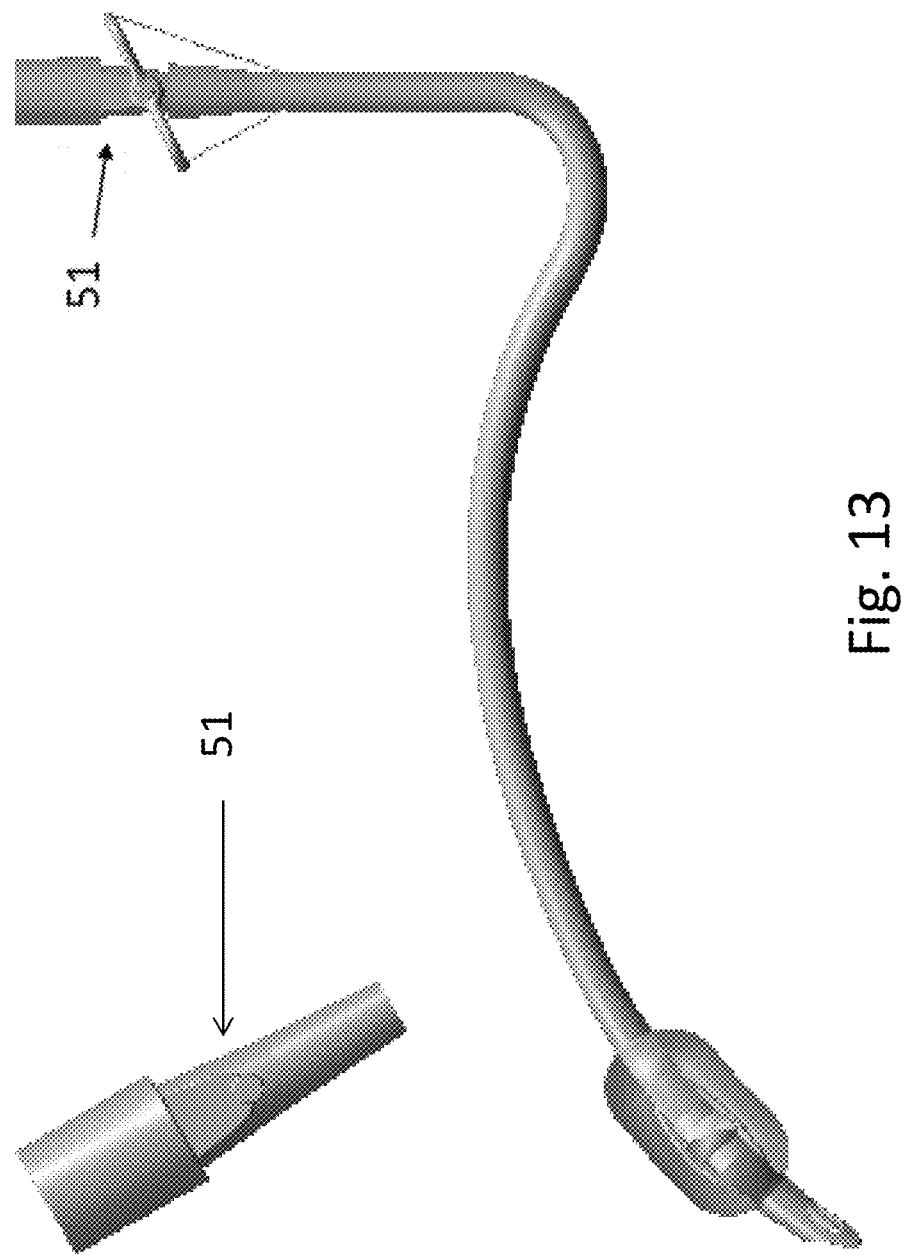
FIG. 13 may show an exemplary embodiment of a bidirectional articulable nasal R.A.E. endotracheal tube with a connector that has two pivots.
Figure 14:
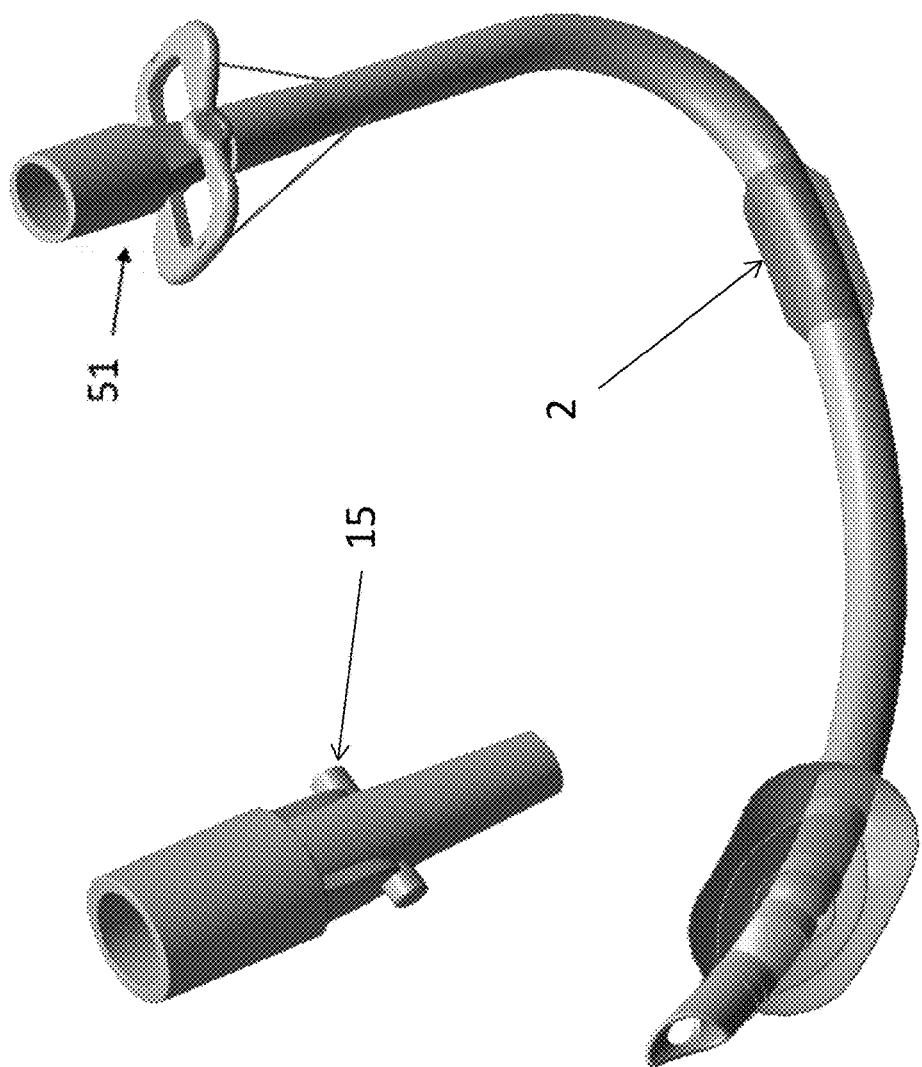
FIG. 14 may show an exemplary embodiment of a bidirectional articulable oral R.A.E. endotracheal tube with a connector that has two pivots.
Figure 15:
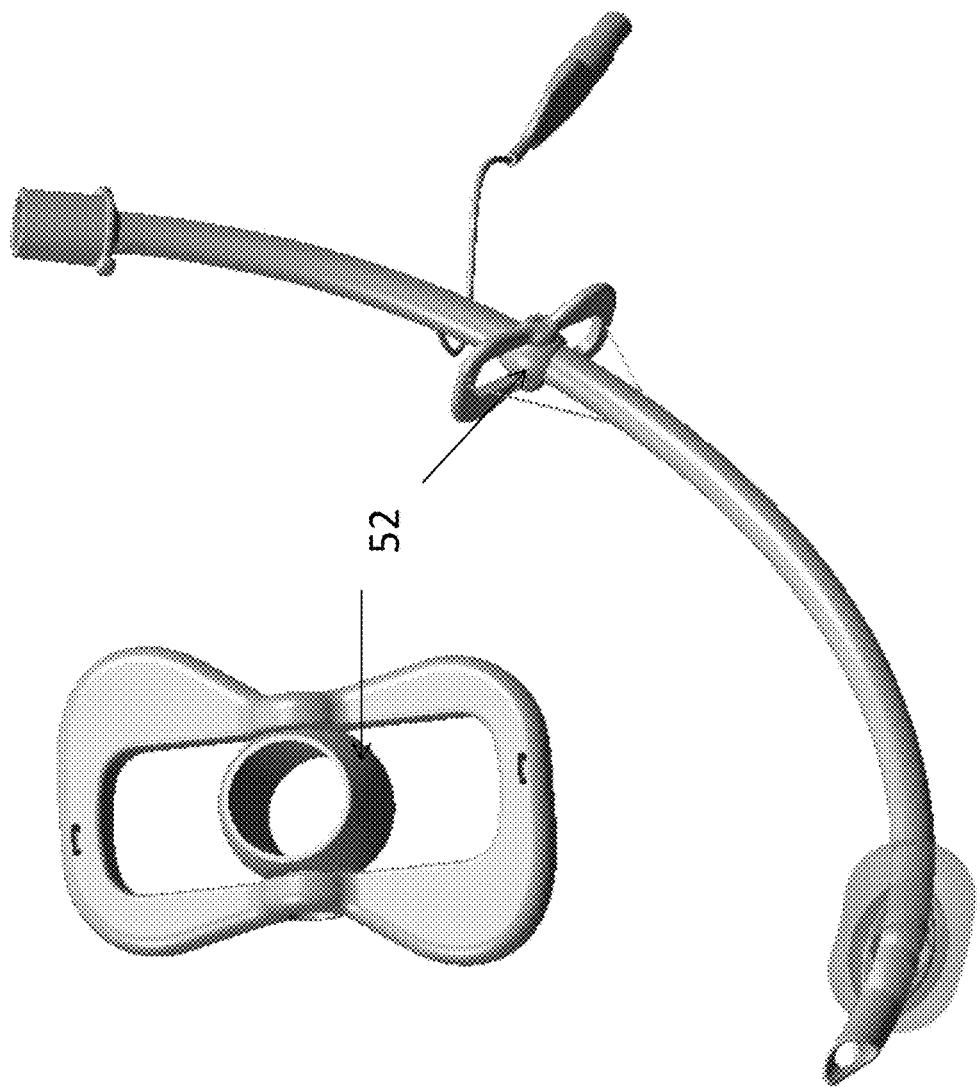
FIG. 15 may show an exemplary embodiment of a bite-block free articulator.

FIGS. 12-15 may represent extension of the articulator-articulee design of the present invention to special types of endotracheal tubes, such as the reinforced, the nasal and oral R.A.E., and finally to bite-block free tubes. FIG. 12 may demonstrate that the design can be readily incorporated to manufacture the reinforced endotracheal tubes, wherein coating of spiral fine wires on the interior surface of tube lumen has no hindrance to the installment of articulator, nor would it to the effect of articulee should the wire coating 50 terminate before endotracheal tube cuff seal 35. FIGS. 13 and 14 may disclose a connector 51 that adds a pair of pivots to connector 10, onto which mounts lever 1. It may suit the special applications of nasal (FIG. 13) and oral (FIG. 14) R.A.E. tubes. Finally, FIG. 15 shows the articulator can be simplified to bite-block free 52, should such endotracheal tubes be desirable under the circumstances.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An endotracheal tube, comprising:
    an elongated tube with a distal end configured to be placed inside a trachea and a proximal end connectable to a ventilator, the tube having a concave and a convex surface which correspond to a patient's anterior and posterior side, respectively;
    a plurality of longitudinal passages having predetermined diameters extending within the tube, each of the plurality of longitudinal passages configured to receive an at least one controlling wire therethrough;
    a bite block having a predetermined length positioned along the tube, the bite block having a first surface and a second surface that align with the convex and concave surfaces of the tube and at least one fulcrum;

at least one opening formed in the first and second surfaces of the bite block, the at least one opening configured to receive the at least one controlling wire;

a removable lever having a ring that removably attaches to the at least one fulcrum and at least one slit that aligns with the at least one opening formed in the first and second surfaces of the bite block, the removable lever controlling a bi-directional movement of the distal end;

a flexible portion of the tube proximate the distal end, the flexible portion comprising:

- a pair of diametric notches with rounded edges formed within the tube and extending through the plurality of longitudinal passages, the diametric notches comprising a first notch proximate the convex surface of the tube and a second notch proximate the concave surface of the tube;
- a first membranous wrap surrounding the diametric notches;
- a first hole and a second hole positioned on opposite sides of the diametric notches and configured to receive the at least one controlling wire;
- a second membranous wrap encompassing the first membranous wrap and the first and second holes; and
- a third membranous wrap encompassing the first and second membranous wraps, the third membranous wrap in fluid communication with at least one of the plurality of longitudinal passages so that air can be injected to inflate the third membranous wrap;

an insertion tip formed at the distal end of the tube; and a connector mounted on the proximal end of the tube, the connector adapted to secure a video imaging stylet to the tube.

2. The endotracheal tube of claim 1, wherein the diametric notches are differently sized, the first notch being larger than the second notch and occupying approximately half of the tube.

3. The endotracheal tube of claim 1, further comprising at least one spacer which separates the diametric notches by at least 1 millimeter.

4. The endotracheal tube of claim 1, wherein the first membranous wrap has a patterned shape with a mid-section that bulges out above the diametric notches disposed underneath.

5. The endotracheal tube of claim 1, wherein the length of the bite block can be reduced to that containing only the at least one fulcrum.

6. The endotracheal tube of claim 1, wherein the bite block is made from two pieces of plastic that are assembled together by mortise-tenon joints.

7. The endotracheal tube of claim 1, wherein the tube has a predetermined diameter.

8. The endotracheal tube of claim 1, further comprising an ultrathin steel cable spirally wired on an interior surface of the tube and extending a length of the tube, the cable providing reinforcement for the tube to prevent crushing and deformation.

9. The endotracheal tube of claim 1, wherein the bite block is constructed from a material that is harder and more rigid than that of the tube.

10. The endotracheal tube of claim 1, wherein the lever has a rectangularly-shaped rim.

11. The endotracheal tube of claim 1, wherein the connector further comprises two connection pivots.

12. The endotracheal tube of claim 1, wherein the connector has a first end having a smaller external diameter that matches an internal diameter of the tube, and a second end having a larger external diameter to correspond with a connector of the ventilator.

13. The endotracheal tube of claim 1, wherein the lever is ergonomically shaped to engage an adult human hand.

14. The endotracheal tube of claim 1, further comprising the at least one controlling wire that extends from the distal end of the tube to the proximal end.

15. The endotracheal tube of claim 14, wherein the controlling the at least one controlling wire is securely fastened in a working position to the lever.

16. The endotracheal tube of claim 1, wherein the lever is color coded to identify endotracheal tubes with different internal dimensions.

17. The endotracheal tube of claim 1, wherein the insertion tip has an upper bevel facing a left vocal cord of a patient, and a lower bevel with a brim shaped in a U-configuration.

18. The endotracheal tube of claim 1, wherein the video imaging stylet further comprises a flexible printed circuit board positioned to span the diametric notches.

19. The endotracheal tube of claim 1, wherein the video imaging stylet performs imaging of a patient's anatomy during intubation.

20. The endotracheal tube of claim 1, wherein the flexible portion of the tube moves bi-directionally via manipulation of the lever.

* * * * *